US008702800B2

(12) United States Patent
Linares et al.

(10) Patent No.: US 8,702,800 B2
(45) Date of Patent: Apr. 22, 2014

(54) MULTI-COMPONENT SHOULDER IMPLANT ASSEMBLY WITH DUAL ARTICULATING SURFACES

(75) Inventors: Miguel A. Linares, Bloomfield Hills, MI (US); Miguel A. Linares, Jr., Bloomfield Hills, MI (US)

(73) Assignee: Linares Medical Devices, LLC, Auburn Hills, MI (US)

(*) Notice: Subject to any disclaimer, the term of this patent is extended or adjusted under 35 U.S.C. 154(b) by 0 days.

(21) Appl. No.: 13/592,738

(22) Filed: Aug. 23, 2012

(65) Prior Publication Data
US 2013/0053970 A1   Feb. 28, 2013

Related U.S. Application Data

(60) Provisional application No. 61/526,388, filed on Aug. 23, 2011, provisional application No. 61/526,404, filed on Aug. 23, 2011.

(51) Int. Cl.
*A61F 2/40* (2006.01)

(52) U.S. Cl.
USPC ...................................... 623/19.13

(58) Field of Classification Search
USPC .................. 623/19.11, 19.12, 19.13, 19.14, 623/22.11–22.46, 23.39–23.41
See application file for complete search history.

(56) References Cited

U.S. PATENT DOCUMENTS

| | | | |
|---|---|---|---|
| 1,051,444 A | 1/1913 | Pleister | |
| 2,314,445 A | 3/1943 | DuVall | |
| 2,667,644 A | 2/1954 | Johnson | |
| 2,821,979 A | 2/1958 | Cameron | |
| 3,694,820 A | 10/1972 | Scales et al. | |
| 3,815,157 A | 6/1974 | Skorecki et al. | |
| 3,916,451 A * | 11/1975 | Buechel et al. | 623/23.4 |
| 3,973,277 A | 8/1976 | Semple et al. | |
| 4,003,095 A * | 1/1977 | Gristina | 623/19.12 |

(Continued)

FOREIGN PATENT DOCUMENTS

| | | |
|---|---|---|
| EP | 1228739 A2 | 8/2002 |
| WO | 9800076 A1 | 1/1998 |
| WO | 2004080331 A2 | 9/2004 |
| WO | 2009039164 A1 | 3/2009 |

OTHER PUBLICATIONS

Tan et al., "Developments of an Antimicrobial Microporous Polyurethane Membrane", Journal of Membrane Science, 289. 199-209 (2007).

*Primary Examiner* — Marcia Hoffman
(74) *Attorney, Agent, or Firm* — Gifford, Krass, Sprinkle, Anderson & Citkowski, P.C.; Douglas J. McEvoy

(57) ABSTRACT

An implant assembly for re-establishing a glenohumeral joint between a scapular and humerus. A ball is adapted to being mounted to a reconditioned glenoid cavity defined in the scapula along with a receiver mounted to a reconditioned humeral head associated with the humerus. A substantially spherical shaped element is interposed between the ball and receiver and establishes first and second articulating surfaces. A concave recess is defined in an exposed face of the ball for seating in articulating fashion a portion of the spherical element. A concave recess is defined in the spherical shaped element for seating in articulating fashion an exposed portion of the scapula mounted ball. Each of the ball, spherical element and receiver is constructed of an alternating material including at least one of a polymer, polymer composite, metal, metal composite or polymer/metal admixture.

2 Claims, 8 Drawing Sheets

(56) References Cited

U.S. PATENT DOCUMENTS

| | | | |
|---|---|---|---|
| 4,040,131 | A | 8/1977 | Gristina |
| 4,045,825 | A | 9/1977 | Stroot |
| 4,206,517 | A * | 6/1980 | Pappas et al. ............ 623/20.13 |
| 4,483,023 | A | 11/1984 | Hoffman, Jr. et al. |
| 4,501,031 | A | 2/1985 | McDaniel et al. |
| 4,665,951 | A | 5/1987 | Ellis et al. |
| 4,693,723 | A | 9/1987 | Gabard |
| 4,744,793 | A | 5/1988 | Parr et al. |
| 4,778,473 | A | 10/1988 | Matthews et al. |
| 4,792,336 | A | 12/1988 | Hlavacek et al. |
| 4,828,562 | A | 5/1989 | Kenna |
| 4,840,630 | A | 6/1989 | Kitamura |
| 4,851,005 | A | 7/1989 | Hunt et al. |
| 4,883,486 | A | 11/1989 | Kapadia et al. |
| 4,906,149 | A | 3/1990 | Rockenfeller et al. |
| 5,004,474 | A | 4/1991 | Fronk et al. |
| 5,078,745 | A | 1/1992 | Rhenter et al. |
| 5,171,325 | A | 12/1992 | Aulie |
| 5,263,984 | A | 11/1993 | Li et al. |
| 5,282,867 | A | 2/1994 | Mikhail |
| 5,376,119 | A | 12/1994 | Zimmermann et al. |
| 5,389,107 | A | 2/1995 | Nassar et al. |
| 5,417,693 | A | 5/1995 | Sowden et al. |
| 5,462,563 | A | 10/1995 | Shearer et al. |
| 5,486,197 | A | 1/1996 | Le et al. |
| 5,507,819 | A | 4/1996 | Wolf |
| 5,554,194 | A | 9/1996 | Sanders |
| 5,571,191 | A | 11/1996 | Fitz |
| 5,575,819 | A | 11/1996 | Amis et al. |
| 5,593,448 | A | 1/1997 | Dong |
| 5,609,647 | A | 3/1997 | Kalberer et al. |
| 5,676,702 | A | 10/1997 | Ratron et al. |
| 5,702,469 | A | 12/1997 | Whipple et al. |
| 5,702,486 | A | 12/1997 | Craig et al. |
| 5,707,395 | A | 1/1998 | Li |
| 5,723,018 | A | 3/1998 | Cyprien et al. |
| 5,728,175 | A | 3/1998 | Rincoe |
| 5,741,335 | A | 4/1998 | Gerber et al. |
| 5,800,566 | A | 9/1998 | Gramnas et al. |
| 5,879,404 | A | 3/1999 | Bateman et al. |
| 5,921,358 | A | 7/1999 | Gramnas et al. |
| 5,961,555 | A | 10/1999 | Huebner |
| 6,001,106 | A | 12/1999 | Ryan et al. |
| 6,010,535 | A | 1/2000 | Shah |
| 6,190,411 | B1 | 2/2001 | Lo et al. |
| 6,193,758 | B1 | 2/2001 | Huebner |
| 6,197,063 | B1 | 3/2001 | Dews |
| 6,245,109 | B1 | 6/2001 | Mendes et al. |
| 6,325,804 | B1 | 12/2001 | Wenstrom, Jr. et al. |
| 6,383,223 | B1 | 5/2002 | Baehler et al. |
| 6,582,715 | B1 | 6/2003 | Barry et al. |
| 6,620,197 | B2 | 9/2003 | Maroney et al. |
| 6,626,942 | B1 | 9/2003 | Edberg et al. |
| 6,645,251 | B2 | 11/2003 | Salehi et al. |
| 6,776,799 | B2 | 8/2004 | Ball et al. |
| 6,790,234 | B1 | 9/2004 | Frankle |
| 6,840,962 | B1 | 1/2005 | Vacanti et al. |
| 6,939,379 | B2 | 9/2005 | Sklar |
| 6,986,790 | B2 | 1/2006 | Ball et al. |
| 7,033,396 | B2 | 4/2006 | Tornier |
| 7,044,983 | B1 | 5/2006 | Cheng et al. |
| 7,056,340 | B2 | 6/2006 | McKernan et al. |
| 7,066,958 | B2 | 6/2006 | Ferree |
| 7,087,091 | B1 | 8/2006 | Chen et al. |
| 7,097,663 | B1 | 8/2006 | Nicol et al. |
| 7,101,398 | B2 | 9/2006 | Dooris et al. |
| 7,153,327 | B1 | 12/2006 | Metzger |
| 7,169,184 | B2 | 1/2007 | Dalla Pria |
| 7,175,663 | B1 | 2/2007 | Stone |
| 7,175,666 | B2 | 2/2007 | Yao |
| 7,189,261 | B2 | 3/2007 | Dews et al. |
| 7,309,360 | B2 | 12/2007 | Tornier et al. |
| 7,329,281 | B2 | 2/2008 | Hays et al. |
| 7,331,995 | B2 | 2/2008 | Eisermann et al. |
| 7,445,638 | B2 | 11/2008 | Beguin et al. |
| 7,462,197 | B2 | 12/2008 | Tornier et al. |
| 7,465,319 | B2 | 12/2008 | Tornier |
| 7,510,558 | B2 | 3/2009 | Tallarida et al. |
| 7,708,781 | B2 | 5/2010 | Scheker |
| 2001/0051831 | A1 | 12/2001 | Subba Rao et al. |
| 2002/0013627 | A1 | 1/2002 | Geistlich et al. |
| 2002/0143402 | A1 | 10/2002 | Steinberg |
| 2003/0130741 | A1 | 7/2003 | McMinn |
| 2004/0024460 | A1 | 2/2004 | Ferree |
| 2004/0039449 | A1* | 2/2004 | Tornier ............ 623/19.13 |
| 2004/0064187 | A1 | 4/2004 | Ball et al. |
| 2004/0064188 | A1 | 4/2004 | Ball et al. |
| 2004/0210317 | A1 | 10/2004 | Maroney et al. |
| 2004/0225370 | A1 | 11/2004 | Cruchet et al. |
| 2004/0267370 | A1 | 12/2004 | Ondrla |
| 2005/0081867 | A1 | 4/2005 | Murphy |
| 2005/0187620 | A1 | 8/2005 | Pai et al. |
| 2005/0192674 | A1 | 9/2005 | Ferree |
| 2005/0261775 | A1 | 11/2005 | Baum et al. |
| 2005/0278032 | A1 | 12/2005 | Tornier et al. |
| 2006/0020344 | A1* | 1/2006 | Shultz et al. ............ 623/19.12 |
| 2006/0058886 | A1 | 3/2006 | Wozencroft |
| 2006/0074423 | A1 | 4/2006 | Alleyne et al. |
| 2006/0111787 | A1 | 5/2006 | Bailie et al. |
| 2006/0149370 | A1 | 7/2006 | Schmieding et al. |
| 2007/0005074 | A1 | 1/2007 | Chudik |
| 2007/0005137 | A1 | 1/2007 | Kwak |
| 2007/0088442 | A1 | 4/2007 | Cima et al. |
| 2007/0179624 | A1* | 8/2007 | Stone et al. ............ 623/19.13 |
| 2008/0234830 | A1 | 9/2008 | Hershberger et al. |
| 2009/0039164 | A1 | 2/2009 | Herwig et al. |
| 2009/0088865 | A1 | 4/2009 | Brehm |
| 2009/0287309 | A1* | 11/2009 | Walch et al. ............ 623/18.11 |
| 2009/0292364 | A1 | 11/2009 | Linares |
| 2011/0098822 | A1* | 4/2011 | Walch et al. ............ 623/19.13 |

* cited by examiner

MULTI-COMPONENT SHOULDER IMPLANT ASSEMBLY WITH DUAL ARTICULATING SURFACES

CROSS REFERENCE TO RELATED APPLICATIONS

The present application claims the priority of U.S. Ser. No. 61/526,388 and U.S. Ser. No. 61/526,404, both filed Aug. 23, 2011.

BACKGROUND OF THE INVENTION

1. Field of the Invention

The present invention is directed to a shoulder implant assembly and, more specifically, to a multi-component implant assembly incorporating a ball and a receiver mounted to first and second shoulder joint defining bones. An optional third substantially spherical shaped and intermediate defining component establishes dual and spaced apart universal and articulating surfaces with the fixedly mounted ball and receiver providing evenly distributed wear profiles for increased useful life of the implant, as well as relieving associated ligament tension.

2. Background of the Relevant Art

The prior art discloses various types of artificial implants, such as replacing damaged natural joint constructions including those for the shoulder. Examples of these include each of the modular humeral head resurfacing system of Winslow et al., US 2006/0009852 and US 2005/0107882, each of which incorporates a two piece humeral component for use in joint arthroplasty which is adapted to be implanted into a joint and engaged by a likewise implanted socket component.

SUMMARY OF THE PRESENT INVENTION

The present invention discloses an implant assembly for re-establishing a glenohumeral joint between a scapular and humerus. The implant includes a ball adapted to being mounted to a reconditioned glenoid cavity defined in the scapula. A receiver is adapted to being mounted to a reconditioned humeral head associated with the humerus.

The substantially spherical shaped element is interposed between the ball and receiver and establishes first and second articulating surfaces. A concave recess is defined in an exposed face of the ball for seating in articulating fashion a portion of the spherical element.

A concave recess is defined in the spherical shaped element for seating in articulating fashion an exposed portion of the scapula mounted ball. Each of the ball, spherical element and receiver is constructed of an alternating material including at least one of a polymer, polymer composite, metal, metal composite or polymer/metal admixture.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

As will be described in additional detail with reference to the succeeding variants, the present invention discloses a multi-component shoulder implant assembly for providing an in-situ and reconditioned installation option which is an improvement over other conventional joint implant installations.

Figure 5:
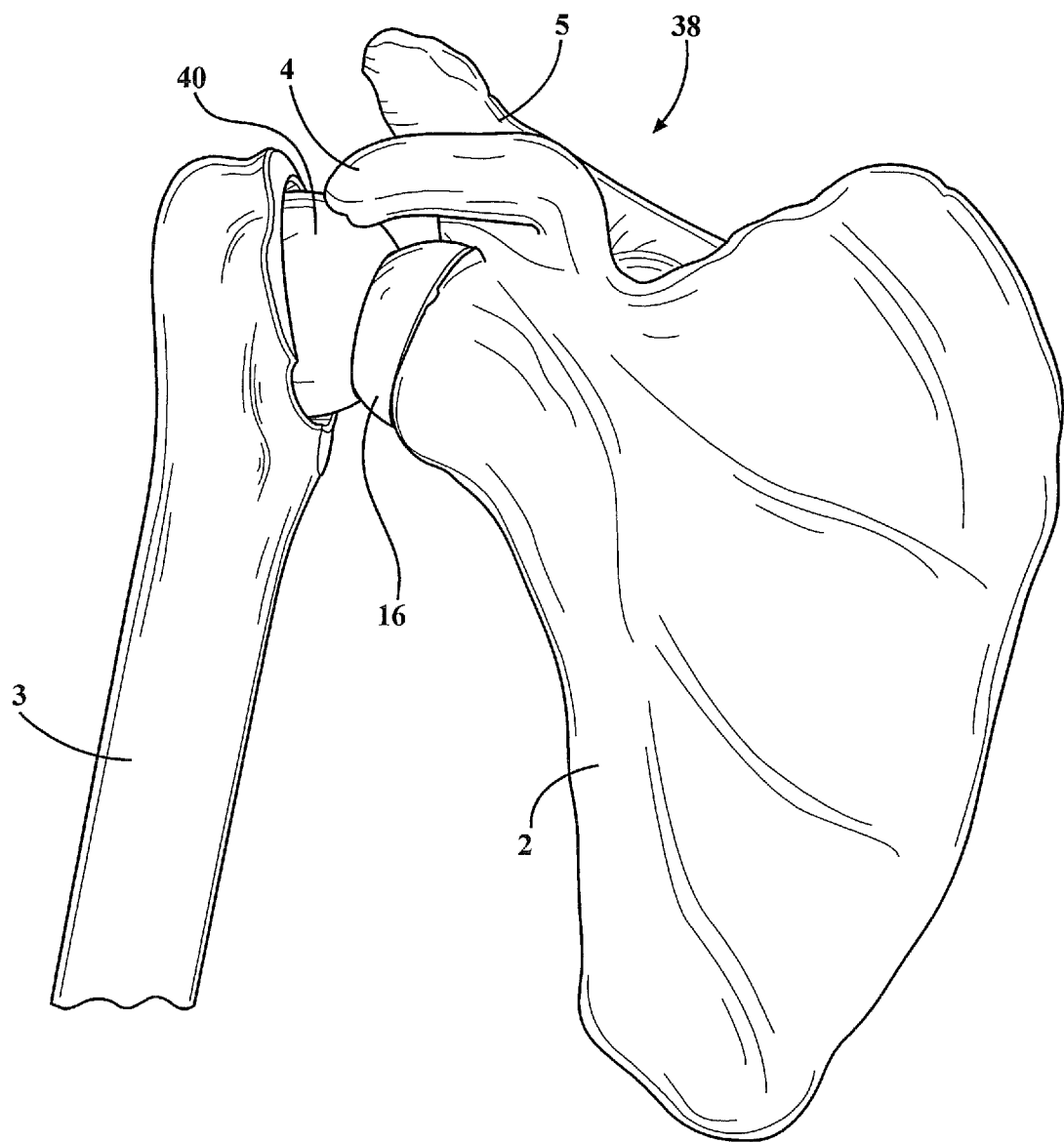
FIG. 5 is an assembled view of a yet further modified shoulder implant assembly exhibiting only first and second scapula and humerus mounted components and eliminating the inter-disposed and supported spheroid shaped component.
Figure 6:
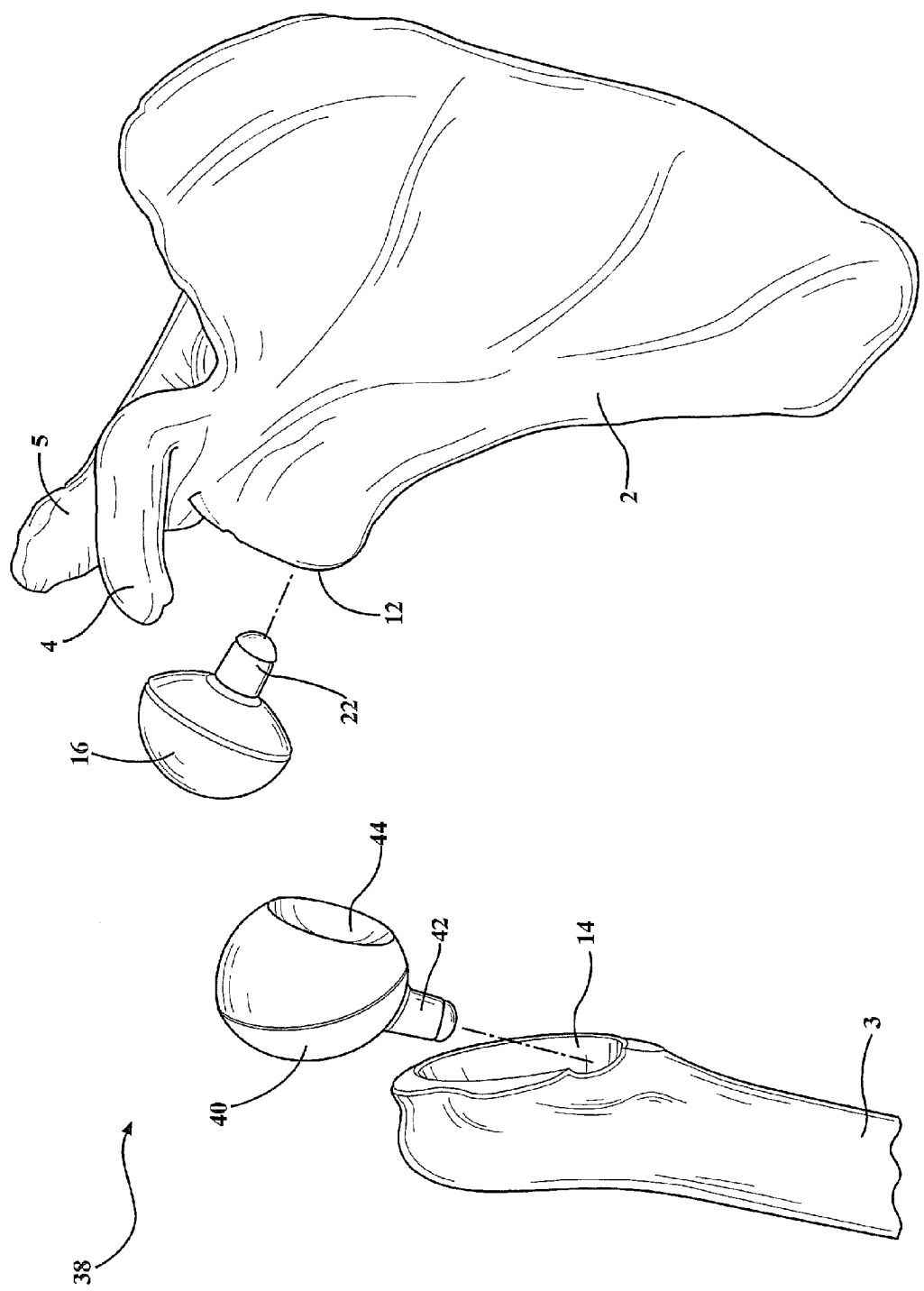
FIG. 6 is an exploded view of the arrangement of FIG. 5 and better depicting the inner concavity profile defined in the humerus mounting receiver and for seating the ball mounted in the scapula.
Figure 7:
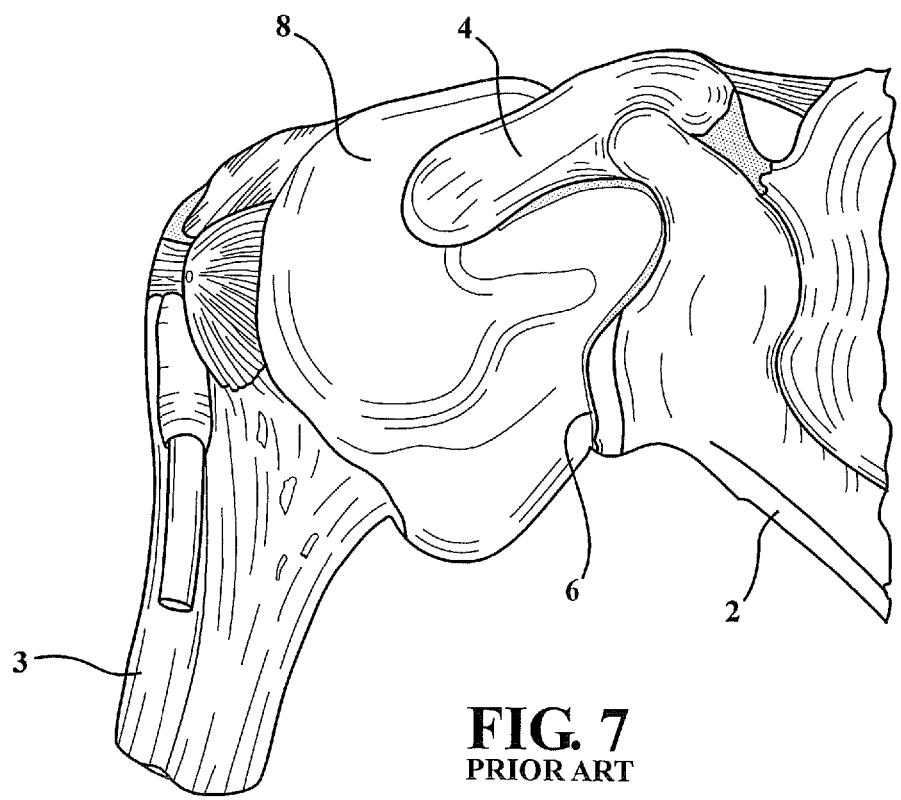
FIGS. 7-9 depict a series of supporting Prior Art illustrations of a human anatomical shoulder joint, and for which the multi-component assembly provides an in situ and reconditioned implantation option.
Figure 9:
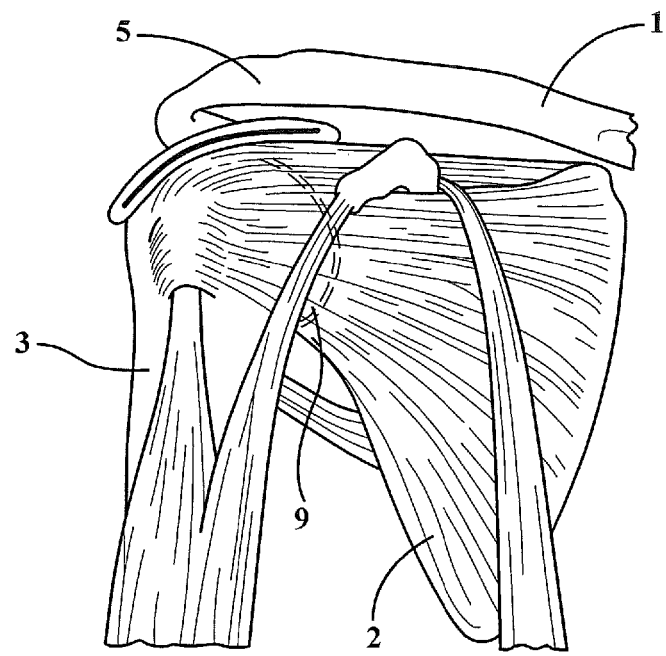
Figure 8:
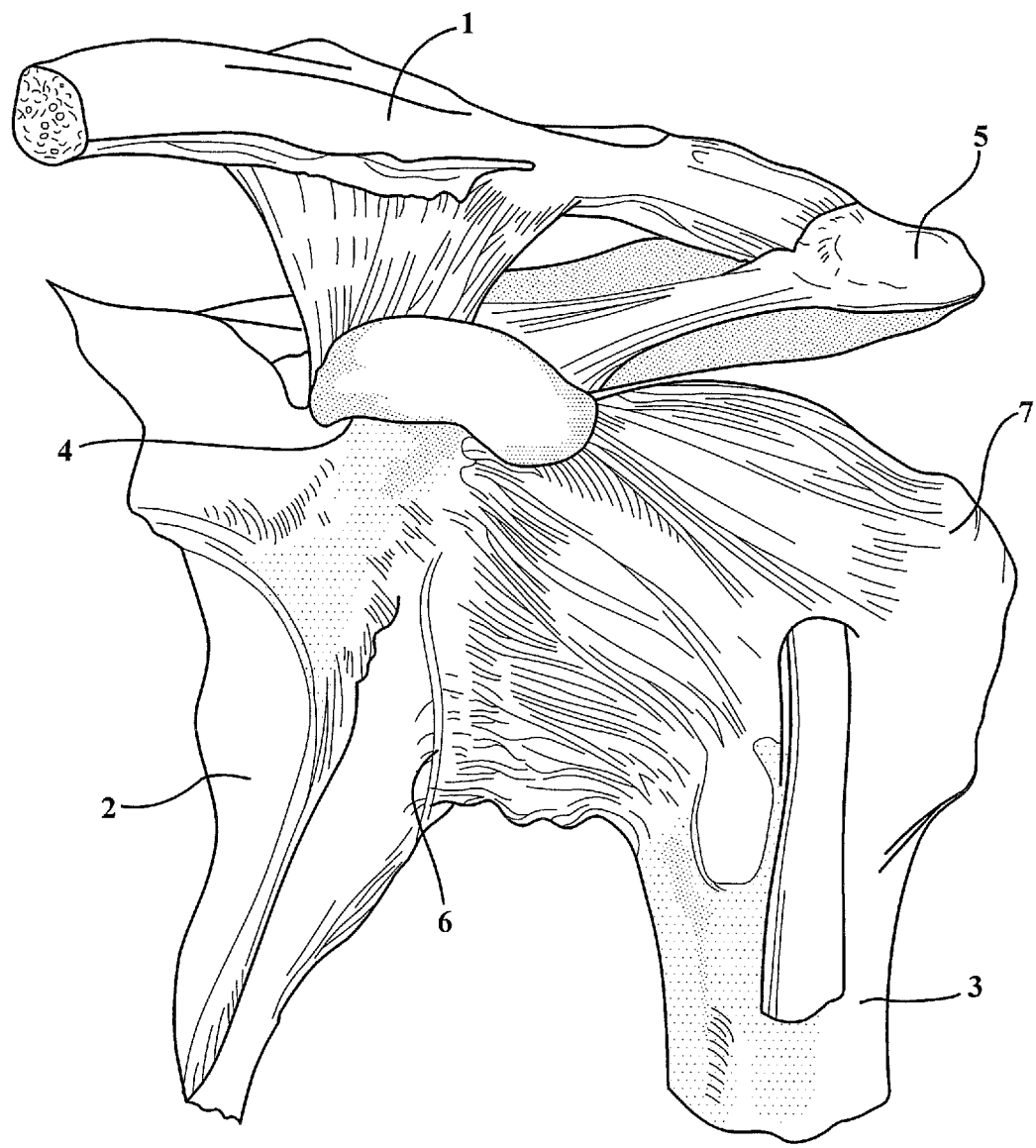

Prior to describing in detail the configurations of the various embodiments of multi-component shoulder implants, respectively depicted in FIGS. 1-2, 3-4 and 5-6, a Prior Art depiction of an anatomically correct human shoulder is shown in FIGS. 7-9 and which includes three bones consisting of the clavicle (collarbone) 1, the scapula (shoulder blade) 2, and the humerus (upper arm bone) 3, as well as associated muscles, ligaments and tendons (see in particular FIGS. 8 and 9). The articulations between the bones of the shoulder collectively make up the shoulder joints where the humerus 3 attaches to the scapula 2.

An abbreviated and incomplete description of the scapula further includes, at strategic locations a coracoid process 4 and spine connected acromion 5, in the proximity of which is configured the glenoid cavity 6. The humerus 3 terminates, in relevant part, at an upper end located humeral head 7 (FIG. 8) which generally seats via an interposed bursa 8 (FIG. 7).

The three joints of the shoulder further include each of the glenohumeral, acromioclavicular and sternoclavicular joints. The glenohumeral joint, see as identified at 9 in FIG. 9, is the main joint of the shoulder and the generic term "shoulder joint" usually refers to this ball and socket joint that allows the arm to rotate in a circular fashion or to hinge out and up away from the body.

As is best depicted in the prior art view of FIG. 8, associated types of joint cartilage include articular cartilage located on the ends of the bones and which allows the bones to glide and move on each other and labrum cartilage located in the shoulder. In combination, the shoulder as constructed exhibits sufficient mobile for undertaking a wide range of actions of the arms and hands as well as being sufficiently stable as to allow for actions such as lifting, pushing and pulling. This compromise between mobility and stability results in a large number of shoulder problems not faced by other joints such as the hip.

With reference now to the embodiments of the invention set forth in FIGS. 1-6, and for purposes of ease and clarity of illustration, a simplified depiction is shown of the glenohumeral joint established between the scapula 2 and humerus 3 and in which all ligaments, muscles and tendons are removed. In each instance, and prior to installation of the multi-component implant assembly (such as occurring after significant degradation of the natural glenohumeral joint or in other instances in which an accident or other traumatic incident has resulted in significant damage), an initial (in situ) surgical reconditioning procedure is employed of the opposing joint defining surfaces established by the humeral head 7 and the glenoid cavity 6. This includes employing relevant surgical drilling and shaping instruments (also not shown) in order to prepare the joint defining locations of the bones for subsequently attaching selected components associated with the implant assembly and as will now be described.

Figure 1:
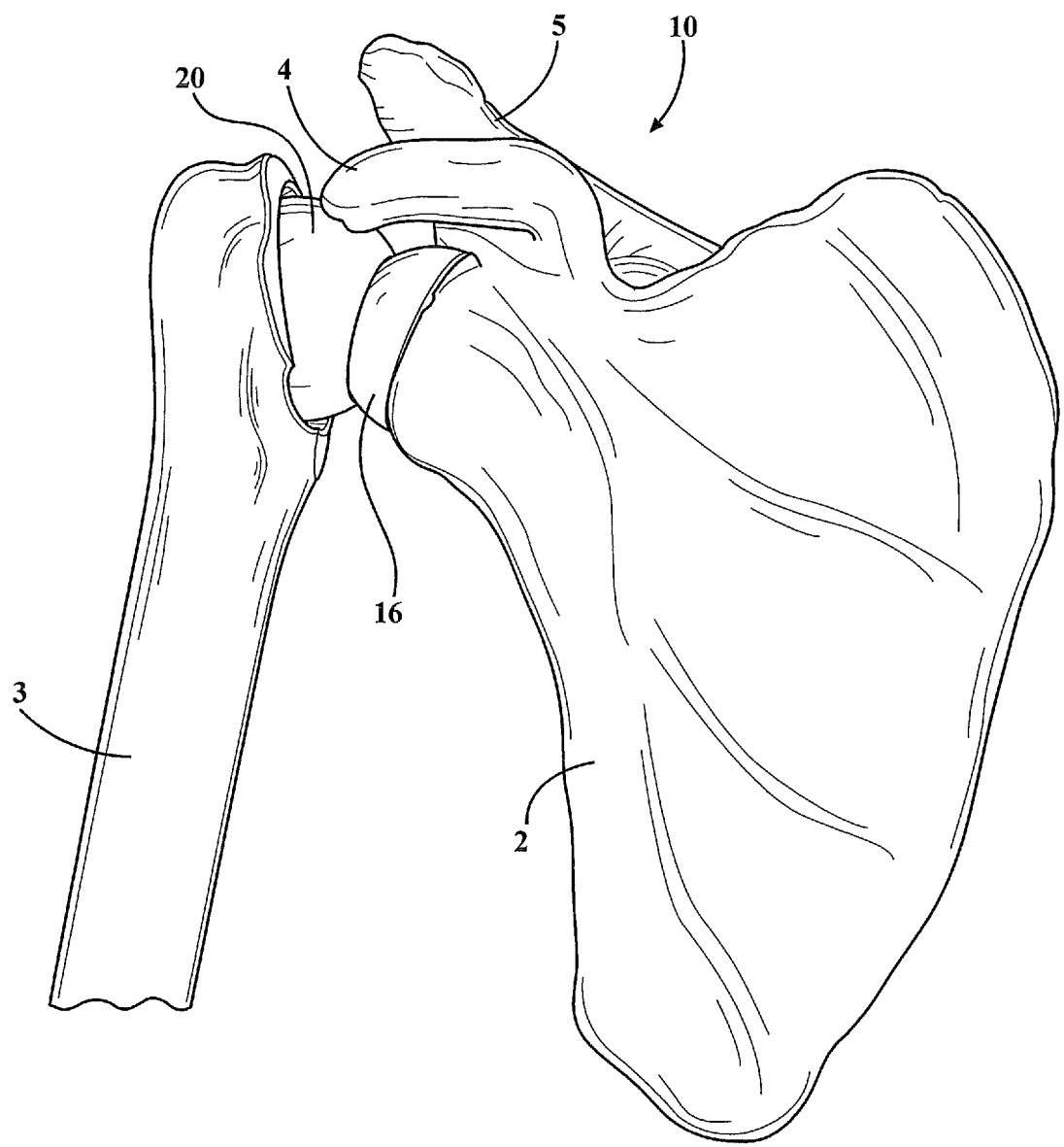
FIG. 1 is an assembled view of a first shoulder implant assembly.
Figure 2:
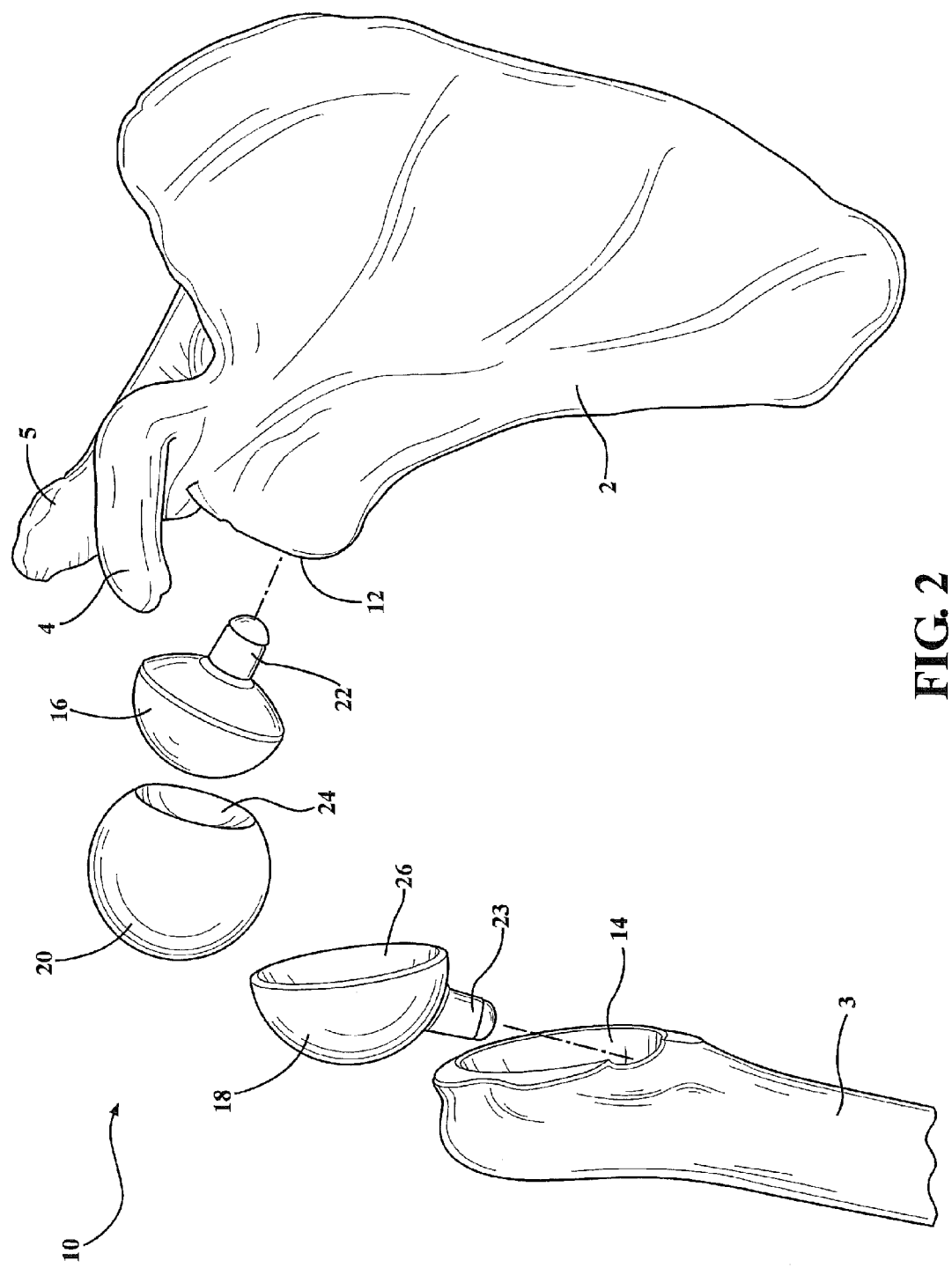
FIG. 2 is an exploded view of the multi-component implant arrangement of FIG. 1 for reconditioned re-engagement of a patient's scapula and upper humerus bones and better depicting the respective mounted ball and receiver components, along with an intermediate and universally inter-supported and substantially spherical shaped component exhibiting an inner concavity profile within which the inner ball seats.

The above stated, and referring initially to each of FIGS. 1 and 2, a pair of assembled and exploded views, both generally at 10, are depicted of a first variant of shoulder implant assembly for installation within reconditioned and opposing end locations of the patient's scapula 2 (represented by reconditioned profile 12) and humerus (further represented by reconditioned profile 14), and as is best shown in the exploded view of FIG. 2. The implant assembly 10 includes, collectively, a stem supported and substantially semi-spherical component, also termed a ball element 16 which is mounted within the reconditioned recess 12 of the scapula glenoid cavity, a likewise stem supported cup 18 mounted within the reconditioned recess 14 of the upper humeral head, and an inter-disposed and substantially spherical shaped element 20 which establishes first and second spaced and articulating surfaces between the ball 16 and receiver 18.

The ball 16, cup 18 and inter-disposed spherical element 20 are each constructed of any suitable material including any type of plastic, metal or admixed composite. While not limited to any specific variant, the material selection for these components can alternate between the components, such as for example the opposite end mounted ball 16 and cup 18 being constructed of a first material (e.g. heavy duty, wear resistant and sanitary polymeric, polymeric composite, surgical steel/aluminum, other metal or metal composite, as well as plastic/metal admixture), and with the inter-disposed spherical element 20 being constructed of a secondary/alternating material selected from such as the other of the identified materials.

The exploded view of FIG. 2 better depicts the configuration of the ball 16, such as exhibiting an outwardly semi-spherical or convex exhibiting end face on a surface thereof, and with a reverse extending stem 22 which seats within a hidden recess configuration (not shown) established within the reconditioned innermost profile 12 of the scapula glenoid cavity, the receiver 18 further exhibiting a likewise extending stem portion 23 which seats within a like configured inner most recess configuration established within the corresponding humeral head reconditioned profile 14. In a typical surgical procedure, a medical bonding cement or other suitable fastener/adhesive (not shown) is employed for anchoring the ball 16 and receiver 18 to the respective bone 2 and 3 ends, it being further understood that the configuration of these elements is capable of being reversed (e.g. the ball 16 mounting to the humeral head and the receiver 18 to the scapula glenoid cavity).

The inter-disposed spherical element 20 depicts a recessed concave profile 24 within which the semi-spherical portion profile of the ball 16 is seated in eccentrically articulating fashion. The humeral head mounted receiver 18 exhibits an enlarged concave profile 26 within which an opposite facing side of the spherical element 20 seats in a likewise eccentrically mounted fashion.

Referring again to the existing arrangement of ligaments, tendons and muscles depicted in the Prior Art views of FIGS. 7-9, these provide the anchoring/seating support for retaining the articulating relationships established between the ball 16 and spherical element 20 and the spherical element 20 and receiver 18, it further being understood that the components 16, 18 and 20 are capable of being retrofit installed within the reconditioned bone ends of the patient without the necessity of the ligaments and tendons being severed of otherwise impacted, thereby enhancing the universal motion profile afforded by the design and likewise reducing recovery time for the patient. As previously described, the ability to segment the articulating motion of the glenohumeral joint into a pair of spaced articulating surfaces serves to both enhance artificial joint mobility as well as to more evenly distribute an associated wear profile of the joint, thereby increasing expected life of the assembly.

Figure 3:
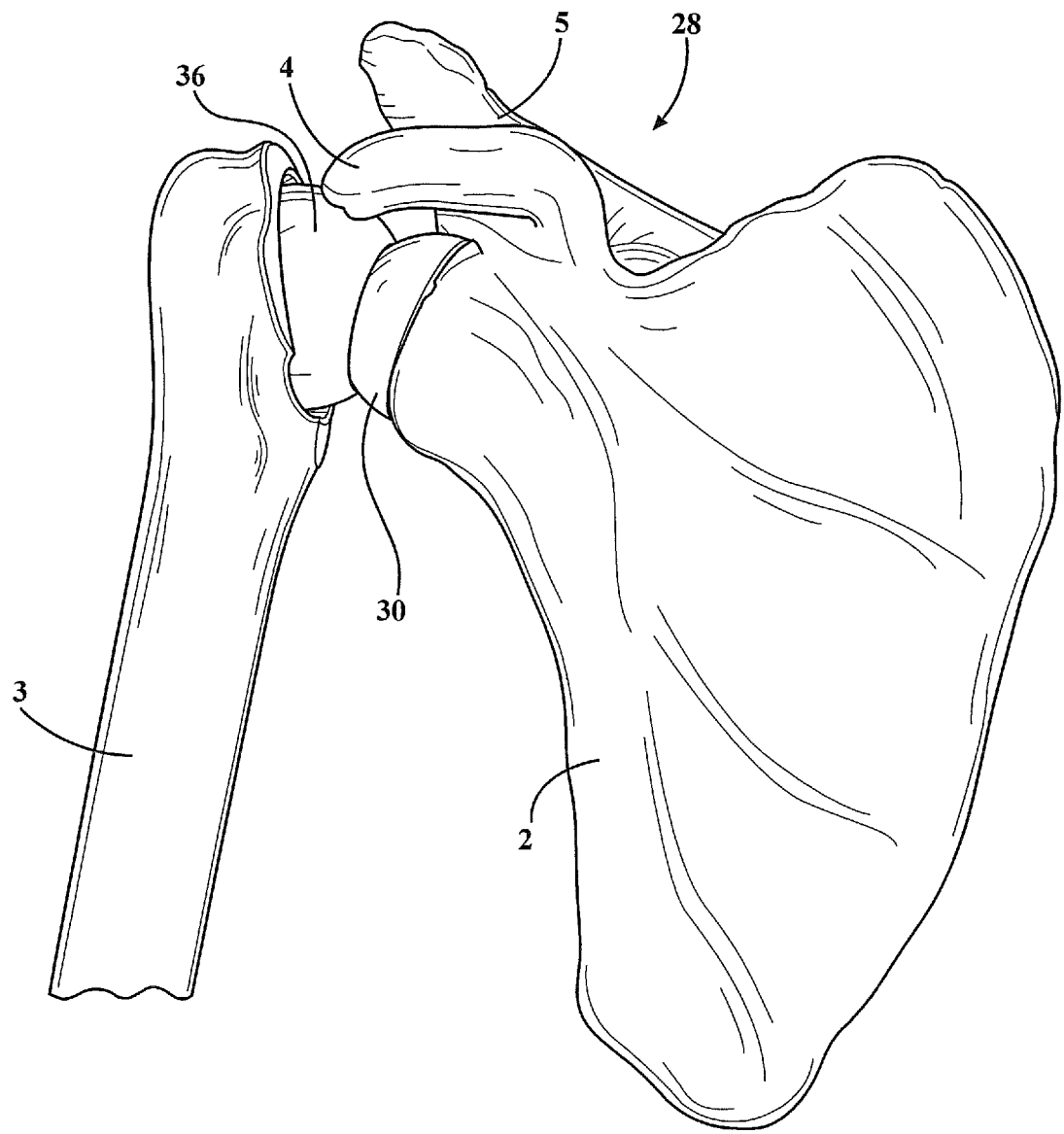
FIG. 3 is an assembled view of a modified shoulder implant assembly.
Figure 4:
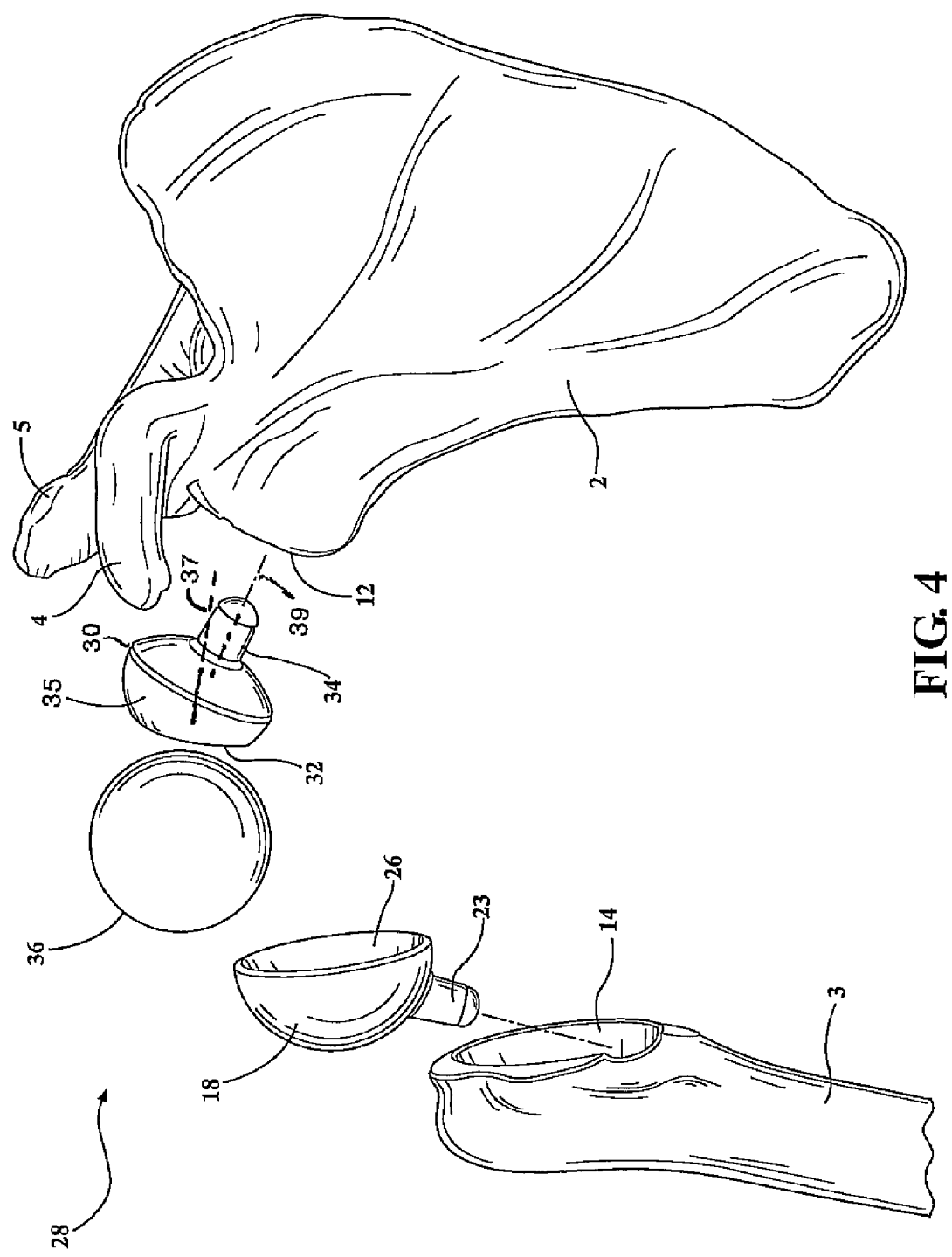
FIG. 4 is an exploded view of the multi-component arrangement of FIG. 3, similar to the previous depiction of FIG. 2, and better illustrating the modified nature of shoulder implant assembly in which the concavity profile is formed in the scapula bone mounted ball component, with the inter-supported element exhibiting a complete spherical shape.

Referring now to FIGS. 3 and 4, respective assembled and exploded illustrations are provided of a related and modified shoulder implant assembly as generally depicted at 28, and in which the humeral head mounted receiver 18 is identical to that previously described. An element depicted at 30 is provided for mounting within the reconditioned glenoid cavity associated with the scapula bone. As clearly shown, the element 30 defines a pseudo-spherical shape exhibiting a first convex bone contacting surface 33, the base terminating in a stem portion 34 extending perpendicularly therefrom such that the base is adaped to mount to the reconditioned glenoid cavity. The element exhibiting a second convex exterior profile 35 (FIG. 4) projecting from the bone surface and such that it includes a recessed concave profile 32 exhibiting only a rim edge therebetween at an outer exposed seating end. A first axis 37 extending through a recessed central location of the concave profile 32 defines an angle (i.e. is not co-linear) relative to a second axis 39 extending through a centerline of the stem portion. A complete spherical shaped inter-disposed element 36 is substituted for the pseudo-spherical element 20 with the concave profile 24 of FIG. 2 and, in combination with the element 30, is seated in a fashion depicted in FIG. 3 upon in-situ installation in which a first convex portion of the spherical element 36 articulates against the recessed concave profile 32 in the element 30, as well as a further convex portion of the element 36 articulating against the concave profile 26 of the receiver 18 as previously described in reference to the description of FIGS. 1-2, and which is substantially identical to the assembly variant of FIG. 1 with the exception of the (hidden) arrangement of the articulating concave profile between the pseudo-spherical shaped element 30 and inter-disposed spherical element 36.

With reference finally to FIGS. 5 and 6, respective assembled and exploded views are shown, generally at 38 of a yet further modified shoulder implant assembly exhibiting only first and second scapula and humerus mounted components and eliminating the inter-disposed and supported spheroid shaped component. Specifically, and as best depicted in FIG. 6, the ball 16 with semi-spherical and convex exterior profile is identical to that previously depicted in FIGS. 1-2, with the receiver being reconfigured, as now shown at 40 to include a slightly modified stem mounting portion 42 and a reduced dimension inner concave profile 44 which is sized for seating directly the increased arcuate angle depicted by the convex profile of the ball 16, and as opposed to such as which is exhibited by the spherical element of the earlier embodiments and not included in this variant.

Having now described our invention, other and additional preferred embodiments will become evident to those skilled in the art to which it pertains, and without deviating from the scope of the appended claims.

We claim:

1. An implant assembly for re-establishing a glenohumeral joint between a scapula and humerus, comprising:
    a pseudo-spherical element having a base with a first convex bone contacting surface, said base terminating in a stem portion extending perpendicularly therefrom such that the base is adapted to mount to a reconditioned glenoid cavity defined in the scapula;
    said element exhibiting a second convex circumferentially extending exterior profile projecting away from the bone surface and a recessed concave profile exhibiting only a rim edge therebetween at an outer exposed seating end of said second convex surface, a first axis extending through a central location of said concave profile defining a non-collinear angle relative to a second axis extending through a centerline of said stem portion;
    a receiver adapted to being mounted to a reconditioned humeral head associated with the humerus, said receiver exposing a second concave profile; and
    a spherical element interposed between said pseudo-spherical element and said receiver a first convex portion of said spherical element articulating relative said recessed concave profile of said pseudo-spherical element, a second convex portion of said spherical element articulating relative said second concave profile of said receiver.

2. The implant assembly as described in claim 1, each of said spherical shaped element, pseudo-spherical shaped element and receiver being constructed of an alternating material including at least one of a polymer, polymer composite, metal, metal composite or polymer/metal admixture.

* * * * *